(12) United States Patent
Uchida

(10) Patent No.: US 6,238,922 B1
(45) Date of Patent: May 29, 2001

(54) USE OF COLLAGENASE IN THE PREPARATION OF NEURAL STEM CELL CULTURES

(75) Inventor: Nobuko Uchida, Palo Alto, CA (US)

(73) Assignee: StemCells, Inc., Sunnyvale, CA (US)

( * ) Notice: Subject to any disclaimer, the term of this patent is extended or adjusted under 35 U.S.C. 154(b) by 0 days.

(21) Appl. No.: 09/258,529

(22) Filed: Feb. 26, 1999

(51) Int. Cl.$^7$ .................................................. C12N 5/02
(52) U.S. Cl. ........................ 435/380; 435/381; 435/378; 435/368
(58) Field of Search .................................. 435/368, 378, 435/380, 381

(56) References Cited

U.S. PATENT DOCUMENTS

| | | | |
|---|---|---|---|
| 4,608,341 | * 8/1986 | Ambesi-Impiombato | 435/240 |
| 5,061,620 | * 10/1991 | Tsukamoto et al. | 435/7.21 |
| 5,270,191 | * 12/1993 | McKay et al. | 435/172.3 |
| 5,342,777 | 8/1994 | Cole et al. | 435/240.31 |
| 5,411,883 | 5/1995 | Boss et al. | 435/240.2 |
| 5,750,376 | * 5/1998 | Weiss et al. | 435/69.52 |
| 5,753,506 | * 5/1998 | Johe | 435/377 |

FOREIGN PATENT DOCUMENTS

| | | |
|---|---|---|
| WO 94/09119 | 4/1994 | (WO). |
| WO 96/04368 | 2/1996 | (WO). |
| WO 96/15226 | 5/1996 | (WO). |
| WO 97/41209 | * 11/1997 | (WO). |

OTHER PUBLICATIONS

Kalyani et al. Developmental Biology. 1997. vol. 186. pp. 202–223.*

* cited by examiner

Primary Examiner—Sandra E. Saucier
Assistant Examiner—Vera Afremova
(74) Attorney, Agent, or Firm—Mintz, Levin, Cohn, Ferris, Glovsky and Popeo, P.C.

(57) ABSTRACT

The invention provides a method for using collagenase to dissociate neural stem cells in neural stem cell cultures when passaging aggregated neural stem cells. The collagenase treatment results in an increased cell viability and an increased number of proliferated neural stem cells over time.

34 Claims, 1 Drawing Sheet

USE OF COLLAGENASE IN THE PREPARATION OF NEURAL STEM CELL CULTURES

FIELD OF THE INVENTION

This invention relates generally to a production or manufacturing process for the in vitro proliferation and culture of neural stem cell cultures using collagenase to dissociate the cultured cells.

BACKGROUND OF THE INVENTION

The development of the mammalian central nervous system (CNS) begins in the early stage of fetal development and continues until the post-natal period. The mature mammalian CNS is composed of neuronal cells (neurons), and glial cells (astrocytes and oligodendrocytes). The first step in neural development is cell birth, which is the precise temporal and spatial sequence in which stem cells and stem cell progeny (i.e. daughter stem cells and progenitor cells) proliferate.

One identifying feature of a stem cell is its ability to exhibit self-renewal or to generate more of itself. A definition of a stem cell is provided by Potten & Loeffler, 110 Development 1001 (1990) who have defined stem cells as "undifferentiated cells capable of (a) proliferation, (b) self-maintenance, (c) the production of a large number of differentiated functional progeny, (d) regenerating the tissue after injury, and (e) a flexibility in the use of these options." The role of stem cells is to replace cells that are lost by natural cell death, injury or disease.

U.S. Pat. Nos. 5,750,376, 5,851,832 (both naming Weiss) and 5,753,506 (Johe), each incorporated herein by reference, refer to in vitro cultures containing neural stem cells. The Weiss patents refer to both suspension and adherent culture, while Johe refers to particular adherent cultures. When the cells are propagated as neurospheres in suspension culture, within 3–4 days in the presence of a proliferation-inducing growth factor, a multipotent neural stem cell begins to divide giving rise to a cluster of undifferentiated cells referred to as a "neurosphere". The cells of a single neurosphere are clonal in nature because they are the progeny of a single neural stem cell. In the continued presence of one or more proliferation-inducing growth factors, such as EGF, bFGF, or the like (and combinations thereof), cells within the neurosphere continue to divide resulting in an increase in the size of the neurosphere and the number of undifferentiated cells. The cells within the neurosphere are immunoreactive for nestin, an intermediate filament protein found in many types of undifferentiated CNS cells. In contrast, mature differentiated cell types derived from the neural stem cell progeny are predominantly negative for nestin.

In the prior art, the cells in the cluster were mechanically dissociated by trituration to produce single cells between passages. Trituration, because it is a mechanical process, exerts shear forces on the cells, that may reduce cell viability between passages. The object of the present invention is to provide an improved culture and manufacture process that increases cell viability from passage to passage and maintains more of the most primitive cells (with the greatest differentiation potential and self-renewal capability).

SUMMARY OF THE INVENTION

The invention provides a method for the in vitro proliferation of multipotent neural stem cell culture using collagenase to dissociate cells in neurospheres between passages. According to the method of this invention, use of collagenase results in improved neural stem cell culture viability, increased number of proliferated cells in those cultures over time, and improved maintenance of cell cultures, as compared with dissociation by trituration or other enzymatic treatments such as trypsinization.

DETAILED DESCRIPTION OF THE INVENTION

Figure 1:
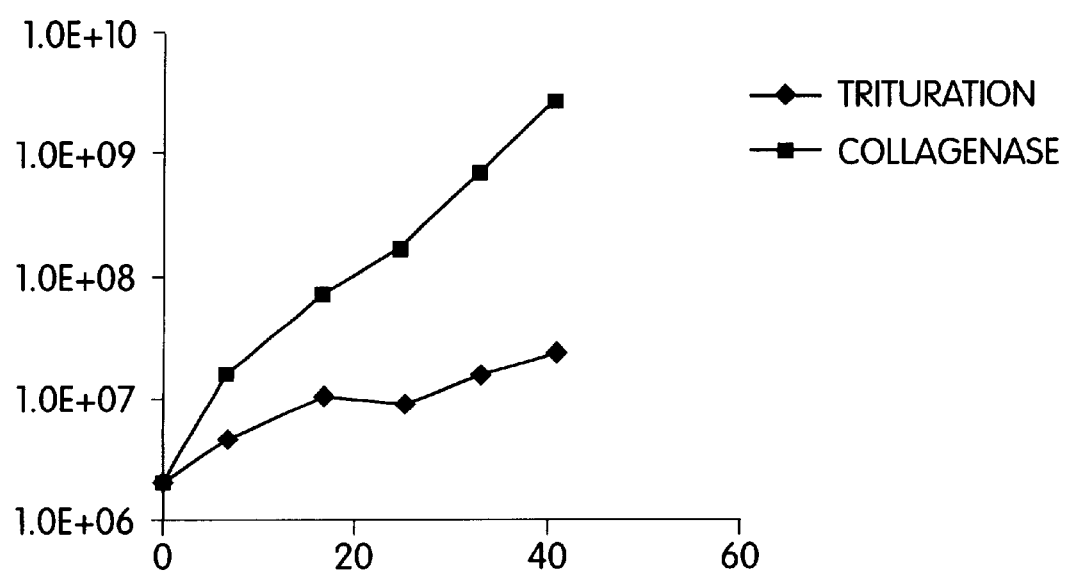
FIG. 1 shows a comparison between the prior art trituration method of dissociating proliferating human neurospheres and the collagenase method of the invention, demonstrating an increased number of viable cells over time using the collagenase method.

Introduction. The invention provides a novel manufacturing process for proliferating neural stem cell cultures, using collagenase to dissociate neurospheres ("aggregated" cells). This method results in an unexpectedly improved neural stem cell culture viability and increased number of proliferated cells over time, as compared with prior art trituration and trypsinization methods for dissociating neural stem cell cultures.

In one embodiment of the collagenase manufacture process, neurosphere cells are harvested and centrifuged (e.g., at 1000 rpm for 3–5 min). After aspirating medium, neurospheres are resuspended collagenase solution (e.g., 1 ml of pre-warmed (37° C.) 0.5 mg/ml), and incubated with the collagenase. After the incubation, cell suspension is diluted in medium and cultured.

In the prior art trituration method, neurosphere cells were harvested and centrifuged. After aspirating medium, neurospheres were resuspended in ~200 $\mu$l of medium. Neurospheres were triturated by using a pipette (e.g., a P200 pipetman with 75 $\mu$l volumes, about 100 times). Then, the cell suspension was diluted in medium and cultured.

Collagenase. Any collagenase which is effective for dissociating neural stem cells in culture may be used in the manufacture process of the invention. "Collagenase" is an enzyme that digests the extracellular matrix protein collagen (Harper, 49 Ann. Rev. Biochem. 1063 (1980)). One source of collagenase is the bacterium *Clostridium histolyticum*. One collagenase assay is a modification of Mandl et al.,32 J. Clin. Invest. 1323 (1953), whereby collagenase is incubated for 5 hr with native collagen. The extent of collagen breakdown is determined using the colorimetric ninhydrin method of Moore & Stein, 176 Biol. Chem 367 (1948). For collagenase unit definition, 1 unit releases one $\mu$mole of L-leucine equivalents from collagen in 5 hr at 37° C., pH 7.5.

Crude collagenases can be used for cell dissociation procedures. Crude collagenase preparations contain not only several collagenases but also a sulfhydryl protease, clostripain, a trypsin-like enzyme, and an aminopeptidase. In some embodiments, we prefer crude collagenase preparations, because of the presence of these additional activities. This combination of collagenolytic and proteolytic activities is effective at breaking down intercellular matrices, the essential part of tissue dissociation. Crude collagenase is inhibited by metal chelating agents such as cysteine, EDTA or o-phenanthroline. It is also inhibited by alpha-2-macroglobulin, a large plasma glycoprotein. $Ca^{2+}$ is thought to be required for enzyme activity.

Commercially-available sources of collagenase are useful in the methods of this invention. For example, purified collagenase contains minimal secondary proteolytic activities, but with high collagenase activity. Purified collagenase can be collagenase H (Cat #1 087 789) from Boerhinger Mannheim (Indianapolis, Ind.). A stock solution of 0.5 mg/ml collagenase is prepared in DPBS containing 0.1% BSA, and stored −20C. Other commercially available sources are Dispase (Boehringer Mannheim), Liberase (Boehringer Mannheim) or collagenase (Serva). The range of collagenase used can be from 100–1000 μg/ml (18–180 mU/ml), preferably between 300–700 μg/ml, (54–126 mU/ml) most preferably about 500 μg/ml (90 mU/ml).

Isolation and In Vitro Proliferation of Multipotent Self-renewing CNS Neural Stem Cells Neurobiologists have used various terms interchangeably to describe the undifferentiated cells of the CNS. Terms such as "stem cell", "precursor cell", and progenitor cell" were once used in the scientific literature. However, there are different types of undifferentiated neural cells, with differing characteristics and fates. The terminology used for undifferentiated multipotent neural cells has evolved such that these cells are now termed "neural stem cells" U.S. Pat. No. 5,750,376 defines the "neural stem" cell proliferated in vitro to mean "an oligopotent or multipotent stem cell which is able to divide without limit and under specific conditions can produce daughter cells which terminally differentiate into neurons and glia." The capability of a cell to divide without limit and produce daughter cells which terminally differentiate into neurons and glia are CNS stem cell characteristics. A CNS neural stem cell is capable of self maintenance, meaning that with each cell division, one daughter cell will also be a stem cell. A CNS neural stem cell can be induced to proliferate using the methods of the present invention.

The non-stem cell progeny of a neural stem cell may include progenitor cells. The progenitor cells generated from a single multipotent self-renewing CNS neural stem cell are capable of differentiating into neurons, astrocytes (type I and type II) or oligodendrocytes. By contrast, the CNS neural stem cell is "multipotent" because its progeny have multiple differentiative pathways.

A "neural progenitor cell" is an undifferentiated cell derived from a multipotent self-renewing CNS neural stem cell, and is not itself a stem cell. Some progenitor cells can produce progeny that are capable of differentiating into more than one cell type. For example, an O-2A cell is a glial progenitor cell that gives rise to oligodendrocytes and type II astrocytes, and thus could be termed a "bipotential" progenitor cell. A distinguishing feature of a progenitor cell is that, unlike a stem cell, it has limited proliferative ability and thus does not exhibit self maintenance. It is committed to a particular path of differentiation and will, under appropriate conditions, eventually differentiate into glia or neurons.

The term "precursor cells" refers to the progeny of multipotent self-renewing CNS neural stem cells, and thus includes both progenitor cells and daughter multipotent self-renewing CNS neural stem cells.

Multipotent self-renewing CNS neural stem cells can be obtained from embryonic, post-natal, juvenile or adult neural tissue. The preferred source neural tissue is from mammals, preferably rodents (e.g., mice and rats) and primates, and most preferably, from humans. Method for the isolation, proliferation, and passaging of multipotent self-renewing CNS neural stem cells from adult human neural tissue, embryonic human neural tissue, adult monkey (Rhesus) neural tissue, mouse embryonic neural tissue, and juvenile and adult mouse brain tissue, including the establishment of neural stem cells in culture from CNS neural stem cells as well as the differentiation of the CNS neural stem cell progeny, are provided by Weiss et al., U.S. Pat. Nos. 5,750,376 and 5,851,832 (each incorporated herein by reference). In the method of the present invention however, neurospheres are collagenase-treated to dissociate the aggregated cells, rather than triturated or trypsinized according to the methods used by Weiss et al., U.S. Pat. No. 5,750,376 and 5,851,832 and Johe, U.S. Pat. No. 5,753,506 (each incorporated herein by reference).

Multipotent self-renewing CNS neural stem cells can be obtained from donor tissue by dissociation of individual cells from the connecting extracellular matrix of the tissue, as described by Weiss et al, U.S. Pat. No. 5,750,376 and 5,851,832 and Johe, U.S. Pat. No. 5,753,506. Tissue is removed from a neural region using a sterile procedure, and the cells are dissociated in tissue culture medium using any method known in the art including treatment with enzymes such as trypsin, collagenase and the like, or by using physical methods of dissociation such as with a blunt instrument, as described by Weiss et al, U.S. Pat. No. 5,750,376 and 5,851,832. Dissociated cells are centrifuged at low speed, between 200 and 2000 rpm, usually between 400 and 1000 rpm, and then resuspended in culture medium. The neural cells can be cultured in suspension or on a fixed substrate. Cell suspensions are seeded in any receptacle capable of sustaining cells, particularly culture flasks, culture plates or roller bottles, and more particularly in small culture flasks such as 25 cm$^2$ culture flasks. Cells cultured in suspension are resuspended at approximately $5 \times 10^4$ to $1 \times 10^6$ cells/ml, preferably $1 \times 10^6$ cells/ml (for 20 week g.w. tissue). Cells plated on a fixed substrate are plated at approximately $2-3 \times 10^3$ 10 cells/cm$^2$, preferably $2.5 \times 10^3$ cells/cm$^2$.

Collagenase-treated neural stem cell cultures, including the multipotent self-renewing CNS neural stem cells of the neurospheres, can be proliferated either on substrates or in suspension, preferably forming clusters of associated undifferentiated cells, referred to as "neurospheres." After culture in the absence of a substrate, the proliferating neurospheres lift off the floor of the culture dish and tend to form the free-floating clusters characteristic of neurospheres. The proliferating precursor cells of the neurosphere continue to proliferate in suspension. The neurospheres of the suspension culture can be easily passaged to reinitiate proliferation. In the method of the invention, individual cells in the neurospheres are separated by collagenase treatment. The collagenase-treated neurosphere cells are then replated at the desired density to reinitiate proliferation. Single cells from the dissociated neurospheres are suspended in culture medium containing growth factor, and a percentage of these cells proliferate and form new neurospheres largely composed of undifferentiated cells. This manufacture process can be repeated to result in a logarithmic increase in the number of viable cells at each passage. The procedure is continued until the desired number of cells is obtained.

Weiss et al., U.S. Pat. Nos. 5,750,376 and 5,851,832 disclose "culture medium containing one or more predetermined growth factors effective for inducing multipotent neural stem cell proliferation." However, different basal media can be used, including, but not limited to:

D-MEM/F12 (Gibco BRL, Gaithersburg, Md.);

Ex Vivo 15 (Bio Whittaker, Walkersville, Md.);

Neural progenitor basal media, (Clonetics. San Diego, Calif.); or combination of the basal media listed above.

The culture medium is supplemented with at least one proliferation-inducing growth factor. As used herein, the term "growth factor" refers to a protein, peptide or other molecule having a growth, proliferative, differentiative, or trophic effect on neural stem cells and/or neural stem cell progeny. Growth factors which may be used for inducing proliferation include any trophic factor that allows neural stem cells and precursor cells to proliferate, including any molecule which binds to a receptor on the surface of the cell to exert a trophic, or growth-inducing effect on the cell. Preferred proliferation-inducing growth factors include members of the EGF superfamily, FGF superfamily, and TGF-α superfamily, such as EGF, amphiregulin, acidic fibroblast growth factor (aFGF or FGF-1), basic fibroblast growth factor (bFGF or FGF-2), transforming growth factor alpha (TGF-α), leukocyte inhibitory factor (LIF), glycostatin C and combinations thereof. A preferred combination of proliferation-inducing growth factors is EGF or TGF-α with FGF-1 or FGF-2. Growth factors are usually added to the culture medium at concentrations ranging between about 1 fg/ml to 1 mg/ml. Concentrations between about 1 to 100 ng/ml are usually sufficient. Simple titration experiments can easily be performed to determine the optimal concentration of a particular growth factor.

The optimization of media formulation permits a higher percentage of neurospheres initiated from primary brain tissue to be established. We prefer Ex Vivo 15 media. The optimization of media formulation also permits a more consistent growth of neurospheres. To maximize neurosphere development, the collagenase-treated neurosphere cells are typically cultured in the presence of LIF, bFGF, EGF, and neural survival factor, NSF (Cat. CC-4323, Clonetics, San Diego, Calif.).

A typical media formulation to culture human neural stem cell cultures is provided in TABLE 1.

TABLE 1

Serum-Free N2/EGF Supplemented Culture Medium For Neural Stem Cell Cultures

| Quantity | Reagents |
| --- | --- |
| 87 ml | DMEM/F12 (Gibco lot. 1012915; Cat No. 11330-032) |
| 1 ml | N-2 Supplement (Gibco lot 1017018; Cat. No. 17502-014) |
| 1 ml | 0.2 mg/ml heparin (Sigma lot 28H0320; Cat. No. H-3149) |
| 1 ml | 0.2 M Glutamine (JCR lot 7N2320; Cat. No. 59202-77p) |
| 10 ml | 3% Glucose (Sigma, lot 37H0841; Cat. No. G-7021) |
| 20 µl | 100 µg/ml EGF (R&D lot CE107091; Cat. No. 236-EG) |
| 100 µl | 20 µg/ml FGF-2 (Gibco lot KCQ411; Cat. No. 13256-029) |
| 100 µl | 10 µg/ml LIF (R&D lot OX038021; Cat. No. 250-L) |

EGF is added to 100 ml base medium for human neural stem cell cultures after filtering the medium. EGF is relatively stable in the medium. FGF-2 and LIF are added when medium is ready to use. The final concentrations of the supplement reagents are:

TABLE 2

| 5 µg/ml | Insulin |
| --- | --- |
| 100 µg/ml | Human transferrin |
| 6.3 ng/ml | Progesterone |
| 16.1 µg/ml | Putrascine |
| 5.2 ng/ml | Selenite |
| 20 ng/ml | EGF |
| 20 ng/ml | FGF-2 |

TABLE 2-continued

| 10 ng/ml | LIF |
| --- | --- |
| 2 µg/ml | heparin |
| 2 mM | L-glumtamine |
| 6 mg/ml | Glucose |

Collagenase-treated neural stem cell cultures can also be differentiated using the differentiation paradigms as described in Weiss et al., U.S. Pat. Nos. 5,750,376 and 5,851,832. For example, (1) collagenase-treated neural stem cell cultures can be differentiated by a rapid differentiation after being plated on poly-L-ornithine-coated glass coverslips in medium containing 0.5% fetal bovine serum (FBS);. (2) collagenase-treated neural stem cell cultures can be differentiated using dissociated neurospheres in EGF-free complete medium containing 1% FBS; (3) collagenase-treated neural stem cell cultures can be differentiated using single neurospheres plated onto laminin-coated glass coverslips; (4) collagenase-treated neural stem cell cultures can be differentiated using single dissociated neurospheres, collagenase-treated, and plated onto a 35 mm culture dish; (5) collagenase-treated neural stem cell cultures can be differentiated using neurospheres co-cultured with striatal astrocytes. In a preferred method of differentiation, neurosphere cells are plated on a laminin coated substrate in the presence of FBS. The resulting differentiated cells are probed by indirect immunocytochemistry for the presence of neuron, astrocytes and oligodendrocytes, for example, using antibodies to MAP-2, tau-1, neurofilament 168 kDa, β-tubulin, GABA, substance P (neuronal markers), GFAP (astrocytic marker), O4, and MBP (oligodendrocyte markers). All three neural cell types are expected to be identified.

Genetic Modification of Collagenase-treated Neural Stem Cell Cultures. The neural stem cell cultures described herein may be genetically modified according to any suitable method known in the art, including in vitro genetic modification, or generation of genetically modified neural stem cell cultures form transgenic mammals. The genetic modification of neural stem cells is performed either by infection with recombinant retroviruses or transfection using methods known in the art (see, Sambrook et al., *Molecular Cloning: A Laboratory Manual* (Cold Spring Harbor Laboratory, N.Y., 1989). Methods of making genetically modified neural stem cells cultures are described, e.g., Weiss, U.S. Pat. No. 5,750,376, incorporated herein by reference.

Generally, the term "genetic modification" refers to the stable or transient alteration of the genotype of a precursor cell by intentional introduction of exogenous DNA. DNA may be synthetic, or naturally derived, and may contain genes, portions of genes, or other useful DNA sequences. The term "genetic modification" includes various gene activation methods known in the art. See, e.g., U.S. Pat. Nos. 5,733,761 and 5,733,746, each herein incorporated by reference.

In certain embodiments the neural stem cells are genetically modified to produce a biologically active molecule, including hormones, enzymes, neurotransmitters, antibodies, cytokines, lymphokines, growth factors, trophic factors, or biological response modifiers. Alternatively the neural stem cells are genetically modified to provide a metabolic or immunologic function upon implantation in a host, preferably a human. It may also be desired to genetically modify cells so they secrete a certain growth factor product. The term "growth factor product" refers to a protein, peptide, mitogen, or other molecule having a growth, proliferative, differentiative, or trophic effect (e.g., NGF, BDNF, the neurotrophins, CNTF, amphiregulin, FGF-1, FGF-2, EGF, TGF-α, TGF-βs, PDGF, IGFs, and the interleukins). Neurosphere progeny cells can also be modified to express a certain growth factor receptor (e.g., p75 low affinity NGF receptor, CNTF receptor, the trk family of neurotrophin receptors, EGF-R, FGF-R, and amphiregulin receptors). Collagenase-treated neural stem cell cultures can be engineered to produce various neurotransmitters, neurotransmitter receptors, or neurotransmitter-synthesizing enzymes.

Transplantation of Neural Stem Cell Cultures to Alleviate Human Disorders.

Collagenase-treated neural stem cell cultures can be produced and transplanted into mammalian hosts, preferably human patients, for the treatment of various disorders, both in the central nervous system ("CNS") and systemically. Cells are delivered to the subject by any suitable means known in the art. If delivered to the central nervous system, then the cells are administered to a particular region using any method which maintains the integrity of surrounding areas of the brain, preferably by injection cannula. Injection methods exemplified by those used by Duncan et al., 17 J. Neurocytology 351–361 (1988), and scaled up and modified for use in humans are preferred. Methods for the injection of cell suspensions such as fibroblasts into the CNS may also be employed for injection of neural precursor cells. Additional approaches and methods may be found in *Neural Grafting in the Mammalian CNS,* Bjorklund & Stenevi, eds. (1985).

Collagenase-treated neural stem cell cultures can be produced and transplanted using the above procedures to treat various neurodegenerative disorders. Such CNS disorders encompass numerous afflictions such as neurodegenerative diseases (e.g. Alzheimer's and Parkinson's), acute brain injury (e.g. stroke, head injury, cerebral palsy) and a large number of CNS dysfunctions (e.g. depression, epilepsy, and schizophrenia). In recent years neurodegenerative disease has become an important concern due to the expanding elderly population which is at greatest risk for these disorders. These diseases, which include Alzheimer's Disease, Multiple Sclerosis (MS), Huntington's Disease, Amyotrophic Lateral Sclerosis, and Parkinson's Disease, have been linked to the degeneration of neural cells in particular locations of the CNS, leading to the inability of these cells or the brain region to carry out their intended function. By providing for maturation, proliferation and differentiation into one or more selected lineages through specific different growth factors the progenitor cells may be used as a source of committed cells. In one series of embodiments, collagenase-treated neural stem cell cultures can be produced and transplanted using the above procedures for the treatment of demyelination diseases. Any suitable method for the implantation of cells near to the demyelinated targets may be used so that the cells can become associated with the demyelinated axons.

Neural stem cell cultures made according to the present invention may also be used to produce a variety of blood cell types, including myeloid and lymphoid cells, as well as early hematopoietic cells (see, Bjornson et al., 283 SCIENCE 534 (1999), incorporated herein by reference).

In Vitro Models of CNS Development, Function and Dysfunction, and Methods for Screening Effects of Drugs on Cells. Collagenase-treated neural stem cell cultures cultured in vitro can be used for the screening of potential neurologically therapeutic compositions. These compositions can be applied to cells in culture at varying dosages, and the response of the cells monitored for various time periods. Physical characteristics of the cells can be analyzed by observing cell and neurite growth with microscopy. The induction of expression of new or increased levels of proteins such as enzymes, receptors and other cell surface molecules, or of neurotransmitters, amino acids, neuropeptides and biogenic amines can be analyzed with any technique known in the art which can identify the alteration of the level of such molecules. These techniques include immunohistochemistry using antibodies against such molecules, or biochemical analysis. Such biochemical analysis includes protein assays, enzymatic assays, receptor binding assays, enzyme-linked immunosorbant assays (ELISA), electrophoretic analysis, analysis with high performance liquid chromatography (HPLC), Western blots, and radioimmune assays (RIA). Nucleic acid analysis such as Northern blots can be used to examine the levels of mRNA coding for these molecules, or for enzymes which synthesize these molecules. Alternatively, cells treated with these pharmaceutical compositions can be transplanted into an animal, and their survival, ability to form neuronal connections, and biochemical and immunological characteristics examined as previously described.

The collagenase-treated neural stem cell cultures can be used in methods of determining the effect of a biological agents on neural cells. The term "biological agent" refers to any agent, such as a virus, protein, peptide, amino acid, lipid, carbohydrate, nucleic acid, nucleotide, drug, pro-drug or other substance that may have an effect on neural cells whether such effect is harmful, beneficial, or otherwise. Biological agents that are beneficial to neural cells are referred to herein as "neurological agents", a term which encompasses any biologically or pharmaceutically active substance that may prove potentially useful for the proliferation, differentiation or functioning of CNS cells or treatment of neurological disease or disorder. To determine the effect of a potential biological agent on neural cells, a culture of collagenase-treated neural stem cell cultures is obtained and proliferated in vitro in the presence of a proliferation-inducing growth factor. Generally, the biological agent will be solubilized and added to the culture medium at varying concentrations to determine the effect of the agent at each dose. The culture medium may be replenished with the biological agent every couple of days in amounts, so as to keep the concentration of the agent somewhat constant.

Thus, it is possible to screen for biological agents that increase the proliferative ability of progenitor cells which would be useful for generating large numbers of cells for transplantation purposes. It is also possible to screen for biological agents which inhibit precursor cell proliferation, using collagenase-treated neural stem cell cultures. Also, the ability of various biological agents to increase, decrease or modify in some other way the number and nature of differentiated neural cells can be screened on collagenase-treated neural stem cell cultures that have been induced to differentiate. The effects of a biological agent or combination of biological agents on the differentiation and survival of differentiated neural cells can then be determined. It is also possible to determine the effects of the biological agents on the differentiation process by applying them to collagenase-treated neural stem cell cultures prior to differentiation.

Other features, objects, and advantages of the invention will be apparent from the description and from the claims.

In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference. The following examples are presented in order to more fully illustrate the preferred embodiments of the invention. These examples should in no way be construed as limiting the scope of the invention, as defined by the appended claims.

EXAMPLE 1

Collagenase Protocol

1. Rinse tissue several times with $Ca^{++}$, $Mg^{++}$-free phosphate buffered saline (PBS).

2. In a Petri dish, cut tissue into 1–2 mm cubed pieces using crossed scalpels. Pour the tissue (packed volume ~7.5 ml) and PBS (~8 ml) into a 50 ml centrifuge tube. Rinse the dish with PBS as necessary to remove tissue, and transfer to the centrifuge tube.

3. Centrifuge the tubes gently to sediment the tissue and free cells (<1000 rpm).

4. Remove the supernatant carefully using a vacuum line.

5. For up to 1.0 g of tissue, add 5.0 ml 0.1% Collagenase, 0.1% Hyaluronidase in HBSS without $Ca^{++}$, $Mg^{++}$ which contains 1.0% bovine serum albumin (BSA).

6. Incubate in 37° C. waterbath with occasional light agitation for 1 hour. At the end of 1 hr, vortex for approximately 3 sec, and evaluate the extent tissue dissociation. If large pieces of intact tissue remains, continue incubation at 37° C. for another 30–45 min. Stand the tube upright for 1–2 min to allow large cell aggregates to settle out. Transfer the supernatant to a fresh tube (1).

7. Top up the fresh tube (1) with PBS+0.1% BSA and centrifuge at approximately 900 rpm for 6 min. Remove the supernatant, which should be cloudy with debris, to a fresh 50 ml centrifuge tube (2). Recentrifige both tubes (1) and (2) at 900 rpm.

8. Discard the supernatant from tube (1) and examine the pellet from tube (2) for viable cells. If worthwhile, combine the pelletted cells from tube (2) with the contents of tube (1). Fill up the tube with PBS+0.1% BSA and respin for 6 min at 900 rpm, discarding the supernatant when finished. Resuspend the cells in PBS and count with trypan blue. At this stage, the cell suspension should be relatively free of debris, and should consist predominantly of healthy cells.

EXAMPLE 2

Collagenase Results

Collagenase treatment provided increased number of viable neural stem cells using the collagenase method. Cells are counted in trypan blue on hemocytometer. A raw count is the number of live cells in defined area.

TABLE 3

|  | Live | Dead | Cells/ml | Total cells | % viability |
|---|---|---|---|---|---|
| Collagenase | 121 | 12 | $8.07 \times 10^5$ | $8.07 \times 10^6$ | 91 |
| Trituration | 45 | 49 | $3 \times 10^5$ | $3. \times 10^6$ | 48 |

Collagenase treatment provided increased number of proliferated neural stem cells over time using the collagenase method.

TABLE 4

| Days | Trituration | Collagenase Treatment | % Viability Trituration | % Viability Collagenase |
|---|---|---|---|---|
| 0 | $2.00 \times 10^6$ | $2.00 \times 10^6$ | | |
| 7 | $4.60 \times 10^6$ | $1.60 \times 10^7$ | 40.00% | 89% |
| 17 | $1.04 \times 10^7$ | $7.28 \times 10^7$ | 52.00% | 93% |
| 25 | $8.80 \times 10^6$ | $1.67 \times 10^8$ | 37.00% | 78% |
| 33 | $1.55 \times 10^7$ | $6.75 \times 10^8$ | 48.00% | 91% |
| 41 | $2.33 \times 10^7$ | $2.61 \times 10^9$ | 38.00% | 98% |
| | | | Average 43.00% ±6.63% | Average 90.% ±7.4% |

TABLE 5

| Days | Trituration | Input Cell No. | Output Cell No. | % Viability | X Expansion | Accumulated Cell No. |
|---|---|---|---|---|---|---|
| 0 | P24-P1 | $2.00 \times 10^6$ | | | | $2.00 \times 10^6$ |
| 7 | P25-P2 | $2.00 \times 10^6$ | $4.60 \times 10^6$ | 40% | 2.3 | $4.60 \times 10^6$ |
| 17 | P26-P3 | $2.00 \times 10^6$ | $4.50 \times 10^6$ | 52% | 2.3 | $1.04 \times 10^7$ |
| 25 | P27-P4 | $2.00 \times 10^6$ | $1.70 \times 10^6$ | 37% | 0.9 | $8.80 \times 10^6$ |
| 33 | P28-P5 | $1.95 \times 10^6$ | $3.00 \times 10^6$ | 48% | 1.8 | $1.55 \times 10^7$ |
| 41 | P29-P6 | $2.00 \times 10^6$ | $3.00 \times 10^6$ | 38% | 1.5 | $2.33 \times 10^7$ |
| | | | | Average 43% | | |

TABLE 6

| Days | Collagenase | Input Cell No. | Accumulated Cell No. | % Viability | X Expansion | Accumulated Cell No. |
|---|---|---|---|---|---|---|
| 0 | P24-P1 | $2.00 \times 10^6$ | | | | $2.00 \times 10^6$ |
| 7 | P25-P2 | $2.00 \times 10^6$ | $1.60 \times 10^7$ | 89% | 8.0 | $1.60 \times 10^7$ |
| 17 | P26-P3 | $2.00 \times 10^6$ | $9.70 \times 10^6$ | 93% | 4.6 | $7.28 \times 10^7$ |
| 25 | P27-P4 | $2.00 \times 10^6$ | $4.60 \times 10^6$ | 78% | 2.3 | $1.67 \times 10^8$ |

TABLE 6-continued

| Days | Collagenase | Input Cell No. | Accumulated Cell No. | % Viability | X Expansion | Accumulated Cell No. |
|---|---|---|---|---|---|---|
| 33 | P28-P5 | $1.70 \times 10^6$ | $8.06 \times 10^6$ | 91% | 4.0 | $7.94 \times 10^8$ |
| 41 | P29-P6 | $2.00 \times 10^6$ | $5.73 \times 10^6$ | 98% Average 90% | 3.9 | $2.27 \times 10^9$ |

The foregoing description has been presented only for the purposes of illustration and is not intended to limit the invention to the precise form disclosed, but by the claims appended hereto.

We claim:

1. A method for the in vitro proliferation of a neural stem cell culture comprising the steps of:
   (a) obtaining dissociated neural tissue in cell suspension, the suspension containing one or more multipotent neural stem cells capable of producing progeny that are capable of differentiating into neurons and glia;
   (b) culturing the cell suspension in a culture medium containing at least one proliferation-inducing growth factor to proliferate the neural stem cells in (a) to generate a neural stem cell culture comprising aggregated neural stem cells; and
   (c) passaging the cell culture in (b) by treating the culture with an amount of a collagenase preparation effective to dissociate the aggregated neural stem cells in the culture and passing the cell culture to a culture medium containing at least one proliferation-inducing growth factor to further proliferate the neural stem cell culture.

2. The method of claim 1 wherein the amount of the collagenase preparation is between 18–180 mU/ml.

3. The method of claim 1 wherein the amount of the collagenase preparation is between 54–126 mU/ml.

4. The method of claim 1 wherein the collagenase preparation further comprises at least one molecule selected from the group consisting of sulfhydryl protease, clostripain, aminopeptidase, or combinations thereof.

5. The method of claim 1 wherein the collagenase preparation is substantially pure, and contains minimal secondary proteolytic activity.

6. The method of claim 1, wherein the proliferation-inducing growth factor is selected from the group consisting of epidermal growth factor, amphiregulin, acidic fibroblast growth factor, basic fibroblast growth factor, transforming growth factor alpha, leukocyte inhibitory factor (LIF), glycostatin C and combinations thereof.

7. The method of claim 1 wherein the neural stem cell culture comprises genetically modified neural stem cells.

8. The method of claim 1, further comprising the step of differentiating the neural stem cell culture of (c) to produce a cell culture comprising differentiated neural cells selected from the group consisting of astrocytes, neurons, oligodendrocytes, and combinations thereof.

9. The method of claim 1 or claim 8, further comprising contacting the neural stem cell culture with a biological agent, and determining the effects of the biological agent on cells in the culture.

10. The method of claim 1 wherein the neural stem cell culture is a suspension culture.

11. The method of claim 1 wherein the neural stem cell culture is an adhesion culture.

12. The method of claim 1 wherein the neural stem cell culture comprises human neural stem cells.

13. A method for the in vitro proliferation of a neural stem cell culture comprising the steps of:
   (a) obtaining dissociated neural tissue in cell suspension, the suspension containing one or more multipotent neural stem cells capable of producing progeny that are capable of differentiating into neurons and glia;
   (b) culturing the cell suspension in a culture medium containing at least one proliferation-inducing growth factor to proliferate the neural stem cells in (a) to generate a neural stem cell culture comprising aggregated neural stem cells; and
   (c) passaging the cell culture in (b) by treating the culture with an amount of a collagenase preparation effective to dissociate the aggregated neural stem cells in the culture and passing the cell culture to a culture medium containing at least one proliferation-inducing growth factor to further proliferate the neural stem cell culture, wherein the percent viability of the cells in the culture is at least 60% after being passaged.

14. The method of claim 13, wherein the percent viability of the cells in the culture is at least 75% after being passaged.

15. The method of claim 13, wherein the percent viability of the cells in the culture is at least 85% after being passaged.

16. The method of claim 13, wherein the amount of the collagenase preparation is between 18–180 mU/ml.

17. The method of claim 13, wherein the amount of the collagenase preparation is between 54–126 mU/ml.

18. The method of claim 13, wherein the collagenase preparation further comprises at least one molecule selected from the group consisting of sulfhydryl protease, clostripain, aminopeptidase, or combinations thereof.

19. The method of claim 13, wherein the collagenase preparation is substantially pure, and contains minimal secondary proteolytic activity.

20. The method of claim 13, wherein the neural stem cell culture comprises genetically modified neural stem cells.

21. The method of claim 13, further comprising the step of differentiating the neural stem cell culture of (c) to produce a cell culture comprising differentiated neural cells selected from the group consisting of astrocytes, neurons, oligodendrocytes, and combinations thereof.

22. The method of claim 13 wherein the neural stem cell culture is a suspension culture.

23. The method of claim 13 wherein the neural stem cell culture is an adhesion culture.

24. The method of claim 13 wherein the neural stem cell culture comprises human neural stem cells.

25. A method for expanding a neural stem cell culture comprising the steps of:
   (a) culturing a neural stem cell culture that contains aggregated multipotent neural stem cells capable of producing progeny that are capable of differentiating into neurons and glia in a culture medium containing at least one proliferation-inducing growth factor to proliferate the culture; and (b) passaging the cell culture in (a) by treating the culture with an amount of a collagenase preparation effective to dissociate the aggregated neural stem cells in the culture and passing the cell culture to a culture medium containing at least one proliferation-inducing growth factor to further proliferate the neural stem cell culture, wherein there is at least a three-fold increase in cell number between weekly passages.

26. The method of claim 25 wherein there is at least a five-fold increase in cell number between weekly passages.

27. The method of claim 25 wherein the neural stem cell culture is a suspension culture.

28. The method of claim 25 wherein the neural stem cell culture is an adhesion culture.

29. The method of claim 25 wherein the neural stem cell culture comprises human neural stem cells.

30. A method for expanding a neural stem cell culture comprising the steps of:

(a) culturing a neural stem cell culture that contains aggregated multipotent neural stem cells capable of producing progeny that are capable of differentiating into neurons and glia in a culture medium containing at least one proliferation-inducing growth factor to proliferate the culture; and (b) passaging the cell culture in (a) by treating the culture with an amount of a collagenase preparation effective to dissociate the agregated neural stem cells in the culture and passing the cell culture to a culture medium containing at least one proliferation-inducing growth factor to further proliferate the neural stem cell culture, wherein the accumulated cell number can be expanded from $10^6$ cells to at least $10^9$ cells in less than 49 days.

31. The method of claim 30 wherein the accumulated cell number can be expanded from $10^6$ cells to at least $10^9$ cells in less than 42 days.

32. The method of claim 30 wherein the neural stem cell culture is a suspension culture.

33. The method of claim 30 wherein the neural stem cell culture is an adhesion culture.

34. The method of claim 30, wherein the neural stem cell culture comprises human neural stem cells.

* * * * *